(12) United States Patent
McKinnie

(10) Patent No.: US 7,408,088 B1
(45) Date of Patent: Aug. 5, 2008

(54) PROCESS FOR SEPARATION OF BROMINE FROM GASEOUS HYDROGEN BROMIDE AND USE OF SUCH PROCESS IN PRODUCTION OF DECABROMODIPHENYLETHANE

(75) Inventor: Bonnie Gary McKinnie, Magnolia, AR (US)

(73) Assignee: Albemarle Corporation, Richmond, VA (US)

(*) Notice: Subject to any disclaimer, the term of this patent is extended or adjusted under 35 U.S.C. 154(b) by 0 days.

(21) Appl. No.: 11/840,321

(22) Filed: Aug. 17, 2007

Related U.S. Application Data

(60) Provisional application No. 60/888,897, filed on Feb. 8, 2007.

(51) Int. Cl.
C07C 17/00 (2006.01)
C07C 22/00 (2006.01)
(52) U.S. Cl. .............. 570/206; 570/190; 570/182
(58) Field of Classification Search .......... None
See application file for complete search history.

(56) References Cited

U.S. PATENT DOCUMENTS

| | | | |
|---|---|---|---|
| 3,752,856 A | 8/1973 | Nagy et al. | |
| 3,965,197 A | 6/1976 | Stepniczka | |
| 4,847,428 A | 7/1989 | Gu | |
| 5,008,477 A | 4/1991 | Hussain | |
| 5,030,778 A | 7/1991 | Ransford | |
| 5,077,334 A | 12/1991 | Hussain | |
| 5,124,496 A | 6/1992 | Templeton et al. | |
| 5,302,768 A * | 4/1994 | Hussain | 570/185 |
| 5,324,874 A | 6/1994 | Ransford et al. | |
| 5,401,890 A | 3/1995 | Parks | |
| 5,457,248 A * | 10/1995 | Mack et al. | 570/206 |
| 5,741,949 A | 4/1998 | Mack | |
| 6,008,283 A | 12/1999 | Rose et al. | |
| 6,518,468 B1 | 2/2003 | Parks et al. | |
| 6,603,049 B1 | 8/2003 | Parks et al. | |
| 6,768,033 B2 | 7/2004 | Parks et al. | |
| 6,841,702 B2 | 1/2005 | Magdolen et al. | |
| 6,958,423 B2 | 10/2005 | Parks et al. | |
| 6,974,887 B2 | 12/2005 | Parks et al. | |
| 7,129,385 B2 | 10/2006 | Dawson et al. | |
| 2003/0144563 A1 | 7/2003 | Falloon et al. | |
| 2004/0110996 A1 | 6/2004 | Parks et al. | |

FOREIGN PATENT DOCUMENTS

| | | |
|---|---|---|
| CA | 2094469 | 9/2005 |
| CN | 1429800 | 7/2003 |
| DE | 2400455 A1 | 2/1975 |
| DE | 2950877 A1 | 6/1981 |
| DE | 3326343 | 1/1985 |
| EP | 0107978 A1 | 5/1984 |
| EP | 0347116 A2 | 12/1989 |
| EP | 0445595 A2 | 9/1991 |
| EP | 0571859 A1 | 12/1993 |
| GB | 981833 | 1/1965 |
| GB | 1411524 | 10/1975 |
| GB | 2143521 | 2/1985 |
| JP | 50018430 | 2/1975 |
| JP | 52039639 | 3/1977 |
| JP | 52139033 | 11/1977 |
| JP | 53053629 | 5/1978 |
| JP | 53116332 | 10/1978 |
| JP | 54044623 | 4/1979 |
| JP | 58222043 | 12/1983 |
| JP | 62004241 | 1/1987 |
| JP | 10158202 | 6/1998 |
| JP | 10175893 | 6/1998 |
| WO | WO 93/24434 A1 | 12/1993 |
| WO | WO 94/22978 A1 | 10/1994 |
| WO | WO 03/055832 A1 | 7/2003 |

OTHER PUBLICATIONS

Yang, Ze-hui, et al., "Technological Progress in Catalytic Synthesis of Decabromodiphenyl Ether by Brominating Diphenyl Oxide with Bromine Chloride", Fine Chemicals, vol. 19, Jan. 2002, pp. 42-44, abstract only translated.

Albemarle Corporation, XP002458574, Saytex 8010 Flame Retardant, Brochure, 2001, 2 pages.

* cited by examiner

Primary Examiner—Karl J Puttlitz

(57) ABSTRACT

Bromine is scrubbed from a gaseous mixture of bromine and hydrogen bromide by passing the mixture into a mixture formed from (i) diphenylethane and/or partially brominated diphenylethane with average bromine number less than about 2 and (ii) a catalytic quantity of iron and/or iron halide in which the halogen atoms are bromine atoms and/or chlorine atoms. Component (i) is brominated, and during such bromination, the mixture is kept hot enough to melt the organics to provide a liquid phase in the scrubber. Gaseous mixtures of bromine and hydrogen bromide are formed in processes of the invention in which decabromodiphenylethane products are produced using the partially brominated diphenylethane as feed to the bromination, which is conducted using an aluminum-based catalyst. Effective ways of removing iron catalyst residues from partially brominated diphenylethane or from decabromodiphenylethane product are also described.

30 Claims, No Drawings

PROCESS FOR SEPARATION OF BROMINE FROM GASEOUS HYDROGEN BROMIDE AND USE OF SUCH PROCESS IN PRODUCTION OF DECABROMODIPHENYLETHANE

REFERENCE TO RELATED APPLICATION

This application claims the benefit and priority of U.S. Provisional Application No. 60/888,897, filed Feb. 8, 2007, the disclosure of which is incorporated herein by reference.

BACKGROUND

Decabromodiphenylethane (DBDPE), 1,2-bis(pentabromophenyl)ethane, is a time-proven commercial flame retardant for use in many flammable macromolecular materials, e.g. thermoplastics, thermosets, cellulosic materials and back coating applications.

Among prior processes for effecting bromination of diphenylethane (DPE) are those described in U.S. Pat. Nos. 5,457,248; 6,518,468; 6,958,423; 6,603,049; 6,768,033; and 6,974,887. The catalysts of choice in conducting such brominations are aluminum catalysts such as aluminum powder and aluminum trihalides in which the halogen is chlorine and/or bromine, and iron catalysts such as iron powder or iron trihalides in which the halogen is chlorine and/or bromine.

While the bromination process can be conducted in various ways, it is desirable to carry out the process in an excess of liquid bromine as the reactant and reaction medium. In such processes, a substantial portion of the major coproduct of the reaction, gaseous hydrogen bromide contains bromine in the vapor state. In order to recover the bromine for reuse, it is necessary to separate the bromine from the gaseous hydrogen bromide. Also, since anhydrous hydrogen bromide is commercially useful as a reactant for producing other chemical products, the removal of bromine from the gaseous hydrogen bromide provides anhydrous hydrogen bromide of sufficient purity for such commercial uses.

Heretofore, gaseous mixtures of bromine and hydrogen bromide have been fed to diphenyl oxide whereby partially brominated diphenyl oxide is formed. This reaction proceeds readily in the absence of a catalyst when using less than 2 moles of bromine per mole of diphenyl oxide.

BRIEF SUMMARY OF THE INVENTION

This invention involves, inter alia, the discovery of a new method of separating bromine from a gaseous mixture of bromine and hydrogen bromide, which method enables achievement of a number of advantages in the overall bromination process for producing highly brominated diphenylethane products, i.e., brominated diphenylethanes having an average of six or more bromine atoms on the rings, and especially decabromodiphenylethane products.

Thus, in accordance with one embodiment of this invention, there is provided a process of removing bromine from a gaseous mixture of molecular bromine and hydrogen bromide, which process comprises passing said gaseous mixture into a mixture having a liquid phase, which mixture is formed from components comprising (i) diphenylethane and/or partially brominated diphenylethane having an average bromine number less than about 2, and (ii) a catalytic quantity of iron and/or at least one iron halide in which the halogen atoms are bromine atoms and/or chlorine atoms, so that component (i) is brominated, and wherein during such bromination, the mixture having a liquid phase is at one or more temperatures at which component (i) and the products formed during the bromination of component (i) are in the liquid state.

In conducting the above process, the mixture having a liquid phase can additionally comprise an inert solvent that is in the liquid state during the process. Preferably, however, the mixture having a liquid phase is formed essentially entirely from components (i) and (ii), and such mixture having a liquid phase is maintained at one or more temperatures of about 110° C. or below that keep the reaction mixture in the liquid state.

Among the features of the above embodiment are that diphenylethane and partially brominated diphenylethane are much more resistant to bromination than diphenyl oxide. Indeed, effective bromination of diphenylethane requires use of a catalyst. In the absence of a catalyst, the reaction proceeds too slowly to effectively remove the bromine and bromination tends to occur on the ethylene bridge rather than on the phenyl groups. Moreover, diphenylethane and partially brominated diphenylethane can be brominated either on the rings or on the ethane bridge and with most Lewis acid bromination catalysts, bromination on the ethane bridge readily proceeds. In the practice of this invention, use of iron or an iron halide catalyst in which the halogen atoms are chlorine or bromine results in exclusive bromination on the aromatic rings of diphenylethane and partially brominated diphenylethane.

Another embodiment of this invention is a process of producing a decabromodiphenylethane product, which process comprises:

I) brominating (A) partially brominated diphenylethane having an average bromine number less than about 4, (B) a mixture of (A) and diphenylethane, or (C) diphenylethane, the bromination being effected with excess bromine in the presence of a Lewis acid bromination catalyst, to produce a decabromodiphenylethane product and wherein a gaseous mixture of hydrogen bromide coproduct containing free molecular bromine is formed, and II) passing said gaseous mixture into a mixture having a liquid phase, which mixture is formed from components comprising (i) diphenylethane and/or partially brominated diphenylethane having an average bromine number less than about 2 and (ii) a catalytic quantity of iron and/or at least one iron halide in which the halogen atoms are bromine atoms and/or chlorine atoms, wherein the mixture having a liquid phase is at a temperature at which (i) is in the liquid state, whereby (i) is brominated so that a partially brominated diphenylethane having an average bromine number less than about 4 is formed, and the amount of bromine in said gaseous mixture is decreased.

The above and other embodiments and features of this invention will be still further apparent from the ensuing description and appended claims.

FURTHER DETAILED DESCRIPTION OF EMBODIMENTS OF THE INVENTION

Glossary

As used anywhere herein including the claims:

A) The term "iron catalyst residue(s)" refers to the residue of the iron or iron halide catalyst remaining after carrying out a bromination of diphenylethane to form a partially brominated diphenylethane (e.g., brominated diphenylethane with an average bromine number of about 2 or less) in excess liquid bromine to which had been added iron and/or an iron halide catalyst in which the halogen atoms are bromine atoms and/or chlorine atoms. The term is not intended to define the chemical composition of the residue other than to indicate that it comprises some form of iron and/or compound(s) of iron that may form during the bromination process.

B) The term "aluminum catalyst residue(s)" refers to the residue of the aluminum or aluminum halide catalyst remaining after carrying out a bromination of diphenylethane to form a decabromodiphenylethane product in excess liquid bromine to which had been added aluminum and/or an aluminum halide catalyst in which the halogen atoms are bromine atoms and/or chlorine atoms. The term is not intended to define the chemical composition of the residue other than to indicate that it comprises some form of aluminum and/or compound(s) of aluminum that may form during such bromination process.

C) Consistent with the above, terms such as "in the form initially utilized" or "as initially charged" or other terms of like import designate that what is being referred to is in the condition or state as it was before being utilized in forming a mixture in which a reaction is to be conducted. Once the material has come in contact with one or more other substances it may or may not retain its initial composition, and such terms do not require that it retain its initial composition or that it loses its initial composition—whatever happens, happens.

D) The term "average bromine number" denotes the average number of bromine atoms on the aromatic ring(s) of a brominated diphenylethane.

Removal of Bromine from Gaseous Mixtures of Bromine and Hydrogen Bromide

As noted above, one embodiment of this invention is a process of removing bromine from a gaseous mixture of bromine and hydrogen bromide, which process comprises passing such mixture into a liquid mixture formed from components comprising (i) diphenylethane (DPE) and/or partially brominated diphenylethane having an average bromine number less than about 2 and (ii) a catalytic quantity of iron which as initially charged, preferably is in subdivided form such as iron powder or iron filings, and/or is at least one iron halide in which the halogen atoms are bromine atoms and/or chlorine atoms, at a temperature at which DPE and/or partially brominated DPE having an average bromine number less than about 2 is in the liquid state. In this process, component (i) is brominated and thus its bromine content increases during the conduct of the process. Typically, this process is conducted in a heated scrubbing vessel into which liquids or solids can be charged, into, through, and out of which gaseous materials can be passed, and from which solids or liquid materials can be readily removed. Ordinarily, the catalytic quantity, expressed as iron, should be in the range of about 100 to about 5000 parts by weight of iron per million parts of DPE and/or partially brominated DPE having an average bromine number less than about 2.

Gaseous mixtures of bromine and HBr which are used as feeds in this bromine removal process can be from any bromination process in which such gaseous mixtures are formed. In accordance with particular embodiments of this invention, such gaseous mixtures are formed during the production of decabromodiphenylethane. Typically, these gaseous mixtures from decabromodiphenylethane production contain in the range of about 0.01 to about 0.1 mole of bromine per mole of HBr.

In the practice of this invention, gaseous mixtures of bromine and HBr are charged into a scrubbing vessel initially containing DPE and/or partially brominated DPE having an average bromine number less than about 2, and iron and/or at least one iron halide catalyst. The temperature in the scrubbing vessel is kept high enough to keep the DPE and partially brominated DPE charged and formed during the operation in the liquid state (i.e., in a molten condition). Typically, the temperature of such liquid mixture will be in the range of about 50 to about 90° C. However, as partial bromination occurs, the melting point of the product mixture decreases and thus the temperature can be further decreased. In fact, with an average of about 0.7 bromine atoms per DPE molecule, the melting point of the partially brominated DPE product mixture has decreased, and thus the reaction temperature at that point can be reduced to about 25° C. Thus, the temperature(s) used should, in any case, be selected to keep the reaction mixture in the molten state, and as indicated, it is possible to reduce the temperature as the average bromine number of the product being formed increases.

In various embodiments of this invention, the scrubber is charged with diphenylethane or partially brominated diphenylethane having an average bromine number of about 1 or less and in the scrubbing process in which bromine is removed from the gaseous mixture of HBr and bromine, the initial diphenylethane or partially brominated diphenylethane is brominated to an average bromine number of up to about 2.

In a batch process for the bromination of DPE to produce a decabromodiphenylethane product, the amount of bromine in the bromine-HBr mixture being returned from the bromination reaction to the scrubbing vessel will produce a partially brominated DPE having an average bromine number of about 2 or less. In other words, the partially brominated DPE will have an average of about 2 or less bromine atoms per molecule of DPE. While an inert solvent can be present as a component of the liquid mixture, it is preferable to charge the scrubbing vessel with undiluted diphenylethane, which can be introduced either in molten form or in solid form. If in solid form, the temperature used in the process should be high enough to convert the solid DPE into molten form.

In a preferred embodiment, molecular bromine is removed from gaseous hydrogen bromide by conducting the above process using diphenylethane as component (i), and in the range of about 100 to about 500 ppm wt/wt (more preferably about 200 ppm wt/wt) based on the weight of the diphenylethane initially present, of iron as anhydrous or hydrated ferric chloride and/or anhydrous or hydrated ferric bromide (e.g., ferric chloride, ferric chloride monohydrate, ferric chloride hexahydrate, ferric bromide, ferric bromide hexahydrate). In addition, the reaction mixture in the scrubbing vessel is preferably maintained at one or more temperatures in the range of about 60 to about 90° C. In most cases, the average bromine number of the resultant partially brominated diphenylethane will be in the range of about 0.4 to about 0.8 bromine atoms, e.g., about 0.6 bromine atoms, per molecule of DPE.

Processes for Producing Decabromodiphenylethane Products

The partially brominated diphenylethanes having an average bromine number of less than about 2 formed in the above processes that remove bromine from gaseous mixtures of bromine and hydrogen bromide can be utilized in producing partially brominated diphenylethane products having an average bromine number of about 6 or more, and preferably decabromodiphenylethane (DPDPE) products. Indeed, this invention can produce decabromodiphenylethane products which, without use of special crystallization or chromatographic separation processes, form decabromodiphenylethane products containing more than 94% of DBDPE. Typically, the balance consists essentially of nonabromodiphenyl ethane ($Br_9DPE$) and, in some cases, octabromodiphenyl ethane ($Br_8DPE$) with the amount of $Br_8DPE$ being less than the amount of $Br_9DPE$. Post reaction washings with water or aqueous bases such as aqueous sodium hydroxide solutions, etc., can be used to remove surface contaminates but such washings do not alter the chemical composition of the product formed directly in the processes. In other words, the products are directly produced in the synthesis process without use of any subsequent procedure to remove or that removes one or more lower brominated diphenyl ethanes from decabromodiphenyl ethane. For the purposes of this invention the % values given for DBDPE and nonabromodiphenyl ethane are to be understood as being the area % values that are derived from gas chromatography analysis. A recommended procedure for conducting such analyses is presented hereinafter.

There are various processes that can be used to produce decabromodiphenylethane products pursuant to this invention. Each of these processes takes advantage of the above-described processes for removing bromine from gaseous mixtures of bromine and hydrogen bromide.

A First DBDPE Production Process Embodiment

One such process embodiment of this invention for producing a decabromodiphenylethane (DBDPE) product (hereinafter sometimes referred to as "first DBDPE production process embodiment" comprises the steps of:

I) brominating a feed of (A) partially brominated diphenylethane having an average bromine number less than about 4, (B) a mixture of (A) and diphenylethane, or (C) diphenylethane, the bromination being effected with excess bromine in the presence of a Lewis acid bromination catalyst, to produce a decabromodiphenylethane product and wherein a gaseous mixture of hydrogen bromide coproduct containing free molecular bromine is formed, and II) passing at least a portion of said gaseous mixture into a mixture having a liquid phase, which mixture having a liquid phase is formed from components comprising (i) diphenylethane and/or partially brominated diphenylethane having an average bromine number less than about 2 and (ii) a catalytic quantity of an iron-based catalyst which, as initially charged, is iron and/or at least one iron halide in which the halogen atoms are bromine atoms and/or chlorine atoms, the mixture having a liquid phase being at a temperature at which (i) is in the liquid state, whereby (i) is brominated to form a partially brominated diphenylethane having an average bromine number of less than about 4, and the bromine content of said gaseous mixture is reduced or eliminated.

In conducting step I) of this first DBDPE production process embodiment, any of a wide variety of process conditions and modes of operation can be employed, provided that the reaction is carried out in excess liquid bromine so that a gaseous mixture of hydrogen bromide coproduct containing free bromine is formed. In one mode of carrying out such a process, at reaction start-up diphenylethane is fed into a reactor containing excess liquid bromine and a Lewis acid bromination catalyst which, as initially charged, is in a form such as finely divided iron, $FeCl_3$, $FeBr_3$, gallium bromide, and other similar Lewis acid bromination catalysts. Preferably the catalyst is an aluminum-based catalyst. The aluminum-based catalyst as initially charged can be in the form of aluminum metal such as aluminum foil, aluminum powder, aluminum turnings, and/or aluminum halide such as aluminum chloride, aluminum bromide, $AlCl_2Br$, $AlBr_2Cl$ or mixtures of two or more such materials. Charging the reactor with aluminum chloride is preferred from an economic standpoint. It appears that during the process the chlorine atoms of the aluminum chloride become displaced by bromine atoms. Typically, the reaction mixture will contain in the range of at least about 14 moles of bromine per mole of DPE and/or partially brominated DPE having an average bromine number of less than about 4 to be fed thereto, and preferably, the reaction mixture contains in the range of about 16 to about 25 moles of bromine per mole of DPE and/or partially brominated DPE having an average bromine number of less than about 4 to be fed thereto. It is possible to use more than 25 moles bromine per mole of DPE and/or partially brominated DPE having an average bromine number of less than about 4. The reaction can be conducted at a refluxing temperature of bromine at atmospheric or elevated pressures, e.g., up to about 40 or 50 psig (ca. $3.77 \times 10^5$ to $4.46 \times 10^5$ Pa). Alternatively, the reaction can be conducted at more elevated pressures such as up to about 60-80 psig (ca. $5.15 \times 10^5$ to $6.53 \times 10^5$ Pa). At atmospheric pressures, the refluxing temperature is in the range of about 57 to about 59° C. but when operating at higher pressures, higher temperatures are used in order to maintain a refluxing condition. Typically, the bromination is conducted at a temperature in the range of about 57 to about 110° C. In order to achieve production of decabromodiphenylethane of high assay by GC and high purity, the feed of DPE and/or partially brominated DPE having an average bromine number of less than about 4 can take place during a period in the range of about 1.5 to about 12 hours, and preferably in the range of about 1.5 to about 3 hours. Since product purity and GC assay are controlled by kinetics, use of higher temperatures in the range of about 70 to about 90° C., e.g., at about 80° C., and at pressures in the range of about 40 to about 80 psig (ca. $3.77 \times 10^5$ to $6.53 \times 10^5$ Pa) are preferred.

Step II) of this first DBDPE production process embodiment utilizes most of the process described above under the heading "Removal of Bromine from Gaseous Mixtures of Bromine and Hydrogen Bromide". In short, the HBr vapor phase containing bromine vapor is passed into a scrubbing vessel charged with (i) diphenylethane and/or partially brominated diphenylethane having an average bromine number less than about 2 and (ii) a catalytic quantity of iron (preferably in subdivided form such as iron powder or iron turnings) and/or an iron halide such as anhydrous $FeCl_3$ or hydrated $FeCl_3$ (e.g., $FeCl_3.H_2O$) or anhydrous $FeBr_3$ or hydrated $FeBr_3$ (e.g., $FeBr_3.H_2O$) with the temperature of this mixture high enough to convert the diphenylethane and/or partially brominated diphenylethane into liquid form. This results in formation of an HBr stream containing a substantially reduced amount of bromine, and partially brominated DPE that has a bromine number of less than about 4 and that contains, inter alia, iron catalyst residue.

In conducting step II) of the first DBDPE production process embodiment, the catalytic quantity of the iron-based catalyst used, expressed as iron, is typically in the range of about 100 to about 5000 parts by weight of iron per million parts of diphenylethane or partially brominated diphenylethane.

In a preferred embodiment, step II) of the first DBDPE production process embodiment is conducted using diphenylethane in lieu of partially brominated diphenylethane, and the amount and identity of the iron catalyst used is in the range of about 100 to about 500 ppm wt/wt (more preferably in the range of about 150 to about 300 ppm wt/wt, and still more preferably about 200 ppm wt/wt) based on the weight of diphenylethane initially present in the scrubbing vessel, of iron as anhydrous or hydrated ferric chloride and/or anhydrous or hydrated ferric bromide (e.g. ferric chloride, ferric chloride monohydrate, ferric chloride hexahydrate, ferric bromide, ferric bromide hexahydrate), or mixtures of any two or more of these, in order to scrub the molecular bromine from the gaseous hydrogen bromide. In most cases, the average bromine number of the resultant partially brominated diphenylethane, when using diphenylethane as the material in the scrubber, will be in the range of about 0.4 to about 0.8 bromine atoms, e.g., about 0.6 bromine atoms, per molecule of DPE.

A Second DBDPE Production Process Embodiment

In another embodiment of this invention, referred to hereinafter as "second DBDPE production process embodiment", decabromodiphenylethane product is produced in a process which comprises:

1) passing a feed of a gaseous mixture of hydrogen bromide and bromine into a mixture having a liquid phase, which mixture having a liquid phase is formed from components comprising (i) diphenylethane and/or partially brominated diphenylethane having an average bromine number less than about 2 and (ii) a catalytic quantity of iron and/or at least one iron halide in which the halogen atoms as initially charged are bromine atoms and/or chlorine atoms, wherein the mixture having a liquid phase is at one or more temperatures at which (i) is in the liquid state, whereby (i) is brominated so that the amount of bromine in said gaseous mixture is decreased, and a reaction mixture comprising partially brominated diphenylethane having an average bromine number less than about 4 and iron catalyst residues is formed;

2) feeding at least a portion of said reaction mixture formed in 1) and optionally diphenylethane to a mixture comprising excess liquid bromine, and a Lewis acid bromination catalyst composed of aluminum and/or aluminum halide in which the halogen atoms in the form initially charged are bromine atoms and/or chlorine atoms, to produce a bromination reaction mixture comprising a decabromodiphenylethane product, molecular bromine, aluminum catalyst and aluminum catalyst residues, and iron catalyst residues, and to produce as a coproduct, a gaseous mixture of hydrogen bromide and molecular bromine;

3) deactivating said aluminum catalyst and removing aluminum catalyst residues and iron catalyst residues from said bromination reaction mixture formed in 2), and recovering decabromodiphenylethane product; and 4) utilizing coproduct gaseous mixture of hydrogen bromide containing molecular bromine as feed in 1).

The reaction conditions used in step 1) above can be any of those utilized in step II) of the first DBDPE production process embodiment described hereinabove. Similarly, the reaction conditions used in step 2) above can be any of those utilized in step I) of the first DBDPE production process embodiment described hereinabove.

Step 3) of this second DBDPE production process embodiment involves work-up of the liquid phase reaction mixture containing the decabromodiphenylethane product solids formed in step 2). Various procedures can be used for such work-up. One such procedure involves adding water to the reaction mixture and distilling the bromine from the reaction mixture, these operations being conducted either in a single vessel or in two separate vessels. Upon completion of the distillation, the remaining reaction mixture—which is acidic because of the presence of residual hydrogen bromide which has been converted to hydrobromic acid upon addition of the water—is cooled or allowed to cool to about 60-70° C. and alkali metal gluconate (preferably sodium gluconate, potassium gluconate, or both) is added in order to chelate the iron. For this purpose, an excess of alkali metal gluconate should be used relative to the amount of iron present. The resultant mixture is then made basic by addition of alkali metal base, such as sodium hydroxide, potassium hydroxide, or both, in order to keep the aluminum catalyst residues in solution. The mixture is then centrifuged or filtered to recover the decabromodiphenylethane product solids. These solids are then washed with water to remove aluminum catalyst residues and other salts from the decabromodiphenylethane product.

In step 4) of this second DBDPE production process embodiment, the coproduct gaseous mixture of hydrogen bromide and bromine is used as feed in step 1) or is included as feed in step 1).

A Third DBDPE Production Process Embodiment

In still another embodiment of this invention, referred to hereinafter as "third DBDPE production process embodiment", decabromodiphenylethane product is produced in a process which comprises:

I) brominating a feed of (A) partially brominated diphenylethane having an average bromine number less than about 4, (B) a mixture of (A) and diphenylethane, or (C) diphenylethane, the bromination being effected with excess bromine in the presence of a Lewis acid bromination catalyst to produce a decabromodiphenylethane product and wherein a gaseous mixture of hydrogen bromide coproduct containing free molecular bromine is formed;

II) passing at least a portion of said gaseous mixture into a liquid mixture formed from components comprising (i) diphenylethane and/or partially brominated diphenylethane having an average bromine number less than about 2 and (ii) a catalytic quantity of an iron-based catalyst which, as initially charged, is iron and/or at least one iron halide in which the halogen atoms are bromine atoms and/or chlorine atoms, the liquid mixture being at a temperature at which (i) is in the liquid state, whereby (i) is brominated to form a reaction mixture comprising partially brominated diphenylethane having an average bromine number of less than about 4 and iron catalyst residues, and the bromine content of said gaseous mixture is reduced or eliminated;

III) removing iron catalyst residues from reaction mixture formed in II); and

IV) utilizing as (A) in I), at least a portion of reaction mixture of III) from which iron catalyst residues have been removed in III).

In this third DBDPE production process embodiment, iron catalyst residues are removed from the partially brominated DPE before using the partially brominated DPE as at least a portion of the feed to the bromination reaction in which decabromodiphenylethane product is formed. In all other respects, the reaction conditions and materials used can be as described with respect to the first DBDPE production process embodiment.

In III) of the third DBDPE production process embodiment, various procedures for removing iron catalyst residues from that reaction mixture can be used. A preferred procedure comprises washing the reaction mixture formed in II) with water to form a two phase mixture. This washing can be conducted at room temperature or at temperatures up to about 100° C. The resultant two phase mixture is then separated to remove the supernatant aqueous phase. The isolated organic phase can then be dried if needed, for example, using calcium chloride. Drying should be utilized if the water content is above about 400 ppm as use of excessively "wet" partially brominated DPE as feed in a bromination reaction can interfere with the bromination reaction.

The use in the third DBDPE production process embodiment of the iron-freed reaction mixture of III) as all or part of the feed in the bromination of I) can also be conducted in various ways. Typically, either the iron-freed reaction mixture of III) will be stored until a sufficient quantity is available for use all at once as the feedstock in I) or, small amounts of the iron-freed reaction mixture will be combined with DPE to form a mixture which is then used as a feedstock in I).

The recommended GC analytical procedure for analysis of a partially brominated DPE with an average bromine number less than about 4 involves injecting 1 microliter of a 10% solution of the product to be analyzed in dibromomethane into a DB-5 capillary column (15 meters×0.53 mm, 1.5 micron film thickness) using split injection and a flame ionization detector. Column conditions used are 40° C. initial temperature, 2 minute hold period at 40° C., and a 10° C. per minute heating rate to increase the temperature to 300° C., with a final time of 5 minutes. The injector and detector are operated at 285° C.

The recommended gas chromatographic procedure for analysis of a decabromodiphenylethane predominant product is as follows. The gas chromatography is conducted on a Hewlett/Packard 5890 Series II equipped with a flame ionization detector, a cool on-column temperature and pressure programmable inlet, and temperature programming capability gas chromatograph using a 12QC5 HTS capillary column, 12 meter, 0.15μ film thickness, 0.53 mm diameter, available from SGE, Inc, part number 054657. Conditions were: detector temperature 350° C., inlet temperature 70° C., heating at 125° C./min to 350° C. with holding at 350° C. until the end of the run, helium carrier gas at 10 mL/min, inlet pressure 4.0 psig (ca. $1.29 \times 10^5$ Pa), increasing at 0.25 psi/min. to 9.0 psig (ca. $1.63 \times 10^5$ Pa) and holding at 9.0 psig until the end of the run, oven temperature 60° C. with heating at 12° C./min to 350° C. and holding for 10 minutes, and injection mode of cool on-column.

DBDPE samples for the recommended gas chromatographic procedure were prepared by dissolving, with warming, 0.003 gram in 10 grams of dibromomethane and injection of 2 microliters of this solution. The integration of the peaks was carried out using Target Chromatography Analysis Software from Thru-Put Systems, Inc. However, other and commercially available software suitable for use in integrating the peaks of a chromatograph may be used. Thru-Put Systems, Inc. is currently owned by Thermo Lab Systems. The address is 5750 Major Blvd., Suite 200, Orlando Fla. 32819. SGE, Incorporated, 2007 Kramer Lane Austin Tex. 78758.

For the Hunter Color Value Test, it is recommended that the solids to be used in the test be samples which have been ground. Thus, samples from a commercial-sized plant are typically samples of product that have been ground in a Raymond mill, a Bepex mill, or equivalent hammer mill. Where the product to be color tested is product from a laboratory scale operation, it is recommended that the analyses be performed on samples that have been ground in a jet mill such as is available from The Jet Pulverizer Company, Inc., model 02-506. The Jet Pulverizer Company's present address is 1255 North Church Street, Moorestown N.J. 08057-1166, and their present mailing address is P.O. Box 212, Palmyra, N.J., 08065-0212. Product samples for comparative testing purposes should be ground under the same conditions whenever possible.

Hunter Color Value determinations are conducted using a HunterLab ColorQuest XE spectrophotometer with appropriate sample devices. The instrument should be standardized for recommended single-number index and the large area of view, first using the light trap then the white standard tile that comes with the instrument. After standardization, the procedure used is as follows:

A) Lower or remove the sample clamp. Install the shelf of the reflectance sample shelf with light cover (HunterLab Part Number B02-1005-172) at the reflectance port.

B) Scoop up powder from the sample batch and fill the 50-mm glass cell (HunterLab Part Number 13-8573-20) to the top. The 2-inch (50-mm) sample thickness makes the translucent powder effectively opaque for reflectance measurements.

C) Tap the sample cup once on a hard surface to settle the loose powder and then place the filled cell flush against the reflectance port so that the powder will be red through the clear glass window of the cell.

D) Cover the sample cell with the opaque cover. The cover minimizes the possibility of ambient light reaching the detector through the powder sample when the measurement is taken.

E) Take a single color reading of the powder. Dump, refill, and read the powder at least three times from the same batch. Average the three color reading for a single color measurement representing the color of the batch. Averaging multiple readings minimizes measurement variation associated with non-uniform samples.

F) Record the average color values for the sample batch.

G) Use ASTM procedure D 1925-87 to calculate Yellowness Index (YI).

The following examples are presented for purposes of illustration. These examples are not intended to limit the scope of this invention to only the conditions described therein.

Example 1

Scrubbing Bromine from Gaseous HBr with DPE and $FeCl_3$ Catalyst

In a 250 mL 3-neck flask with 14/20 joints, equipped with a condenser connected to a water trap, sparging tube, thermocouple, magnetic stirrer, and heated in a water bath were placed 3.1 g $FeCl_3$ and 126.7 g DPE. This, at 60-62° C., was sparged with HBr gas for about 10 minutes then HBr was saturated with $Br_2$ gas, before entering the DPE, by passing the HBr through a flask containing 18.5 mL $Br_2$. The flask containing the $Br_2$ was held in a water bath at room temperature. The HBr flow rate was about 100-200 mL/min. After about 2.5 hours all of the $Br_2$ had been evaporate from its flask. The HBr flow was then stopped. The system was then purged with $N_2$ for 30 minutes and then the DPE reaction mixture was poured into 300 mL water and stirred well. A sample of the organic phase was analyzed by GC using dibromomethane as solvent. GC analysis was on a 15 meter DB-5 column operated at 40° C., hold 2 min., then heated at 10° C. per min. to 300° C. The results are summarized in Table 1.

TABLE 1

| GC Column Retention Time (RT), min | Indicated Compound | Area % |
|---|---|---|
| 2.37 | Benzene | 0.037 |
| 7.53 | Bromobenzene | 0.005 |
| 17.2 | DPE | 60.06 |

TABLE 1-continued

| GC Column Retention Time (RT), min | Indicated Compound | Area % |
|---|---|---|
| 20-21 | Monobromo-DPE | 33.7% (2 peaks) |
| 23.5-24.5 | Dibromo-DPE | 4.9% (3 main peaks) |
| 26-28 | Tribromo-DPE | 0.7% (6 peaks) |

Comments: The indications that the products with RT of 20-21, 23.5-24.5, and 26-28 were monobromo-DPE species, dibromo-DPE species, and tribromo-DPE species, respectively, are supported by the following: NMR analysis of the sample did not indicate the presence of any diphenylethane brominated on the ethane bridge, and did indicate the presence of some bromination in the para position of phenyl groups.

Example 2

Scrubbing Bromine from Gaseous HBr with DPE and Iron & Water as a Catalyst System In the apparatus described in Example 1 were placed 0.226 g of Fe powder and 0.41 g of 60% aqueous HBr, followed by 91.2 g molten DPE. This was heated at 65° C. and HBr (250 mL/min) was sparged in for 30 minutes. The mixture was light yellow in color and not all the Fe had dissolved. The feed of HBr was adjusted so that it passed first into a flask containing 41.7 g of $Br_2$ and then into the DPE mixture. The HBr flow was maintained at 240-250 mL/min. and the reactor containing the DPE was held at 62-66° C. After 3.7 hours all bromine had been evaporated by the HBr gas. HBr flow was continued for about 5 minutes and then the mixture was purged with $N_2$ for about 10 minutes. The water trap was virtually colorless meaning that it contained <10 ppm $Br_2$. A sample of the reaction mixture were taken for NMR and GC analyses. The remainder were poured into water-containing about 4 mL of concentrated HCl. Much of the Fe powder remained unreacted. The pale yellow organic phase was phase separated, washed with water, and dried over $CaCl_2$. The results of GC analysis, carried out as described in Example 1, are summarized in Table 2.

TABLE 2

| GC Column Retention Time (RT), min | Indicated Compound | Area % |
|---|---|---|
| 2.4 | Benzene | 0.02 |
| 7.5 | Bromobenzene | 0.002 |
| 14.2 | DPE | 53.4 |
| 20.59 | Monobromo-DPE | 10.67 |
| 20.79 | " | 0.4 |
| 21.14 | " | 31.0 |
| 23.54 | Dibromo-DPE | 0.36 |
| 24.05 | " | 1.71 |
| 24.58 | " | 2.10 |

Comment: NMR analysis of a sample of the product showed no benzylic bromination had occurred.

Example 3

Scrubbing Bromine from Gaseous HBr with DPE and 100 ppm of Iron as $FeBr_3$ as Catalyst In the flask described in Example 1 were placed 0.050 g $FeBr_3$ and 0.085 g 60% HBr. This was nitrogen purged at a rate of 15 mL/min for about 18 hours. DPE (120 grams) was added and this mixture was stirred at 52-60° C. and HBr was sparged in (250 mL/min) for about 10 minutes. Some of the $FeBr_3$ remained undissolved but the DPE turned dark red. $Br_2$ (17 ml) was added to a vessel through which the HBr passed before entering the DPE reactor. Over about 4.5 hours this bromine evaporated, during which time the reactor containing the DPE was held at 57-64° C. and the HBr at 240-250 mL/min. $N_2$ (250 mL/min) was sparged in for 5 minutes and then 150 mL of water was added. The water trap, 1273 g, contained about 12 ppm $Br_2$, and 13.7% HBr. The reaction mixture, after stirring well, was phase separated and the organic phase was dried over $CaCl_2$. GC of a sample of the organic phase showed the results summarized in Table 3.

TABLE 3

| GC Column Retention Time (RT), min | Indicated Compound | Area % |
|---|---|---|
| 2.4 | Benzene | 0.0118 |
| 7.6 | Bromobenzene | 0.0086 |
| 17.17 | DPE | 56.78 |
| 20.50 | Monobromo-DPE | 9.04 |
| 20.74 | Monobromo-DPE | 0.31 |
| 21.00 | " | 30.48 |
| 23.5 | Dibromo-DPE | 0.22 |
| 24.00 | " | 1.20 |
| 24.52 | " | 1.72 |

Comment: NMR of a sample of the product showed that no benzylic bromination had occurred.

In a procedure similar to that of Example 3, 53.1 grams of bromine was added, as a vapor in HBr gas, to 106.1 grams DPE containing 10 ppm iron, added as $FeBr_3$. The bromine was added at 60-71° C. over 5.5 hrs. NMR analysis (delta 3.5, mulitplet and delta 5.1 triplet) indicated that greater than 90% of the bromination was benzylic rather than aromatic. The GC analysis was inconsistent with Examples 1-3 where aromatic bromination had occurred. It was thus concluded that at least under the conditions used, 10 ppm of iron is insufficient for effectively catalyzing the bromination of DPE in the presence of gaseous HBr.

Example 4

Scrubbing Bromine from Gaseous HBr with DPE and $FeCl_3.6H_2O$ Catalyst

In a 250 mL 3-neck flask equipped with an ⅛-inch (~0.32 cm) O.D. diptube, magnetic stirrer, heating mantle, condenser connected to a water trap, and thermocouple were placed 0.20 g $FeCl_3.6H_2O$ (Mallinckrodt) and 127 g molten DPE. This mixture was sparged with HBr for about 10 minutes during which the mixture turned nearly black. Bromine (20 mL) was placed in a 250 mL round bottom flask and about 200 mL/min HBr was passed through this flask before entering the DPE via the diptube. Initially the temperature of the DPE mixture was 80° C. but during most of the 3.6 hrs of bromine vapor addition the temperature was maintained at 60-64° C. When all 20 mL of bromine had evaporated, the trapped HBr was colorless indicating the absence of $Br_2$. The mixture was $N_2$ purged for about 10 minutes and then 100 mL of water was added to the DPE mixture. The resultant mixture was stirred for 15 minutes at about 50° C. and then phase separated and dried over $CaCl_2$. A sample of the product, bright yellow in color, was subjected to GC analysis, yielding the results summarized in Table 4.

TABLE 4

| GC Column Retention Time (RT), min | Indicated Compound | Area % |
|---|---|---|
| 2.37 | Benzene | 0.024 |
| 17.2 | DPE | 50.6 |

TABLE 4-continued

| GC Column Retention Time (RT), min | Indicated Compound | Area % |
|---|---|---|
| 20.5 | Monobromo-DPE | 10.5 |
| 20.7 | Monobromo-DPE | 0.39 |
| 21.04 | " | 33.27 |
| 23.5 | Dibromo-DPE | 0.35 |
| 24.0 | " | 1.82 |
| 24.5 | " | 2.44 |

Comments: NMR analysis of another sample of the product showed no benzylic bromination. GC-MS confirmed that the peaks at 20.5 to 21.04 min are aromatic brominated monobromo-DPE and the peaks at 23-25 min are aromatic dibromo-DPE where the bromine atoms apparently are on different rings. The calculated approximate average composition of this product is 0.6 atom of bromine per molecule of diphenylethane ($Br_{0.6}$-DPE).

Example 5

Preparation of Decabromodiphenylethane Using DPE Scrubbing of Bromine from Gaseous HBr with $FeCl_3$ Catalyst 1) Scrubbing step—In a 250 mL flask equipped as in Example 4 were placed 0.08 g $FeCl_3$ and 124.4 g DPE. At 57° C., this mixture was sparged with HBr at a flow rate of 200 mL/min for 5 minutes. Then 24 mL of $Br_2$ was added to a flask through which the HBr passed before contacting the DPE. The HBr entered the stirred DPE subsurface via a 1/16-inch (ca. 0.16 cm) I.D., 1/8-inch (0.32 cm) O.D. diptube. The scrubber reaction mixture was kept at 56-60° C. as the mixture of HBr and $Br_2$ was sparged into the mixture. After about 4 hours all $Br_2$ had been evaporated by the HBr. The mixture was sparged with HBr at 200 mL/min for 5 more minutes. Then, the mixture was sparged with nitrogen at a feed rate of 200 mL/min. The contents of the HBr trap, 1272 g, were found to contain 12 ppm of $Br_2$ by analysis using sodium thiosulfate titration. A 0.4 g sample of the DPE reaction mixture was taken for GC analysis. After $N_2$ sparging for 20 minutes as the DPE reaction mixture cooled, the scrubber reactor was placed under a $N_2$ blanket. The GC analysis of the sample of the DPE reaction mixture showed it to contain 42 area % DPE, 300 ppm benzene, 50.0 area % monobromo-DPE isomers, and 7.1% dibromo-DPE isomers.

2) Bromination of Partially Brominated DPE From 1)—A 2-liter flask was equipped with a heating mantle, thermocouple, mechanical stirrer, a water-cooled condenser topped by a 0° C. Friedrich condenser and a 1/4-inch (0.64 cm) O.D. diptube with a 1/16-inch (0.16 cm) O.D. orifice at the end for feeding partially brominated DPE mixed with bromine. Bromine condensate was collected by means of a Dean-Stark trap between the water-cooled condenser and the reactor and used to dilute the partially brominated DPE in the diptube. The two feeds to the diptube were fed by means of peristaltic pumps. The partially brominated DPE was fed down an 1/8" (0.32 cm) O.D. tube that extended to near the bottom of the 1/4-inch diptube and the bromine was fed into the annular space, such that the two mixed in the diptube immediately prior to exiting from the orifice. The reactor was charged with 8.6 g of $AlCl_3$ and 2117 g of liquid bromine. The reactor was brought to reflux and feeding of bromine and partially brominated DPE commenced at the same time. The partially brominated DPE was fed over a period of about 4.5 hours during which time the 13-19 mL/min of condensate bromine were fed to the diptube to dilute the partially brominated DPE. Reaction temperature was 58.9 to 59.7° C. When addition of the partially brominated DPE was complete the mixture was refluxed 5 min. longer then 1000 mL of water added. Bromine was distilled to a reactor temperature of 100° C. The mixture cooled to about 60° C. and 102 g of 25% NaOH was added to the mixture. Analysis of the water in the reactor showed 1.4% NaOH. After adding another 20 g of 25% NaOH, the mixture was filtered and washed with 1 liter of water yielding product in the form of solids, a sample of which, on analysis, was found to have a melting point of 350.5-352° C., and an assay of 99.7 GC area % decabromodiphenyl ethane. After drying the product overnight at 125° C. the product formed weighed 650 g. This was Jet-Milled and then oven-aged for 6 hrs in a 230° C. oven. Analysis then showed 22 ppm iron, 0 ppm aluminum, m.p. 351° C., and color values of Hunter L=92.11, Hunter a=0.26, Hunter b=5.24, and Hunter YI=10.39.

Example 6

Preparation of Decabromodiphenylethane Using DPE Scrubbing of Bromine from Gaseous HBr with $FeCl_3$ Catalyst and Decabromodiphenylethane Product Work-Up with Sodium Gluconate 1) Scrubbing step—Using the procedure as in Example 5, 150.8 g DPE and 0.088 g $FeCl_3$ were reacted with 34 mL of $Br_2$ using 250 mL/min HBr to sweep $Br_2$ vapor into the DPE. The $HBr/Br_2$ feed occurred over 5 hrs at 60-65° C. The mixture was then $N_2$ purged for about 2 minutes then placed under a blanket of $N_2$. A 0.3 g sample of this product was taken for GC analysis, which showed 33.16 area % of DPE, 56.37 area % of monobromo-DPE, and 10.37% dibromo-DPE.

2) Bromination of Partially Brominated DPE From 1)—A 2-liter flask, equipped with mechanical stirrer, thermocouple, 2 condensers in series, and a diptube, all as described in Example 5, was charged with 5.2 g of $AlCl_3$ and 2703 g of $Br_2$. The contents of the reactor were sparged with HBr gas for about 5 minutes to dissolve the $AlCl_3$. After bringing the bromine to reflux, the feeds of bromine and the partially brominated DPE (pb-DPE) was initiated. Bromine condensate was fed to the diptube initially at 10 mL/min but mainly at 19-20 mL/min during the 4.4 hours that partially brominated DPE was fed. The reactor was maintained at 58.4 to 58.8° C. during the addition. It was refluxed 5 min longer then cooled partially and 900 mL water added, then bromine distilled to 100° C. The mixture was cooled to 60° C. then 0.32 g of sodium gluconate in 10 mL of water was added. Then, after stirring well, 65 g of 25% aqueous NaOH was added. Titration of a sample of the water showed 1.13% NaOH. More 25% aqueous NaOH (21 grams) was added, stirred well, then the solids were collected and washed with about 1500 mL of water. After drying at 130° C., a sample, analyzed by GC, showed 0.53 area % $Br_9$-DPE and 99.47% decabromodiphenyl ethane. This product was Jet-Milled then oven aged at 230° C. for 7 hours. Analysis then showed 10 ppm iron, 0 ppm aluminum, m.p. 350° C., and color values of Hunter L=89.94, Hunter a=0.61, Hunter b=5.69, and Hunter YI=11.88.

Example 7

Scrubbing Bromine from Gaseous HBr with DPE and $FeCl_3$

In this run, two 250 mL flasks were connected in series. The first flask was charged with 186.6 g of liquid $Br_2$. The second with 105 g of DPE and 0.18 g of $FeCl_3$ (black). $N_2$, at a rate of about 300 mL/min was swept through the first flask and into the second flask subsurface using a 1/8-inch (0.32 cm) O.D. diptube. All bromine was evaporated from the first flask over a period of 5.2 hours during which time the temperature of the second flask was maintained at 75-80° C. Formation of some solids on walls of the second flask was noted. All solids melted when the temperature was raised to about 95° C. A sample (0.8 g) of the product was taken for GC analysis. The results of this analysis are summarized in Table 5.

TABLE 5

| GC Column Retention Time (RT), min | Indicated Compound | Area % |
|---|---|---|
| 2.25 | Benzene | 39 ppm |
| 7.27 | Bromobenzene | 84 ppm |
| 11.94 | Dibromobenzene | none |
| 16.9 | Diphenylethane | 0.024% |
| 20.7 | Monobromo-DPE | 2.33% |
| 23.24 | Dibromo-DPE | 5.89% |
| 23.8 | " | 34.1% |
| 24.04 | " | 1.43 |
| 24.37 | " | 53.4 |
| 25.8-27.3 | Tribromo-DPE (7 peaks) | 1.4% |

The mixture was allowed to solidify. About 50 mL of water was added to the 250 mL flask, and this was heated slowly to 92° C. to melt all contents. The melt was stirred well, then poured into a bottle. When solidified, the water layer was decanted from the product.

Example 8

Preparation of Decabromodiphenylethane Product from Partially Brominated DPE, and Purification of the Decabromodiphenylethane Product In a 1-liter round bottom flask equipped with a 0° C. Friedrich condenser, a mechanical stirrer, a thermocouple, and a ⅛-inch (0.32 cm) O.D. diptube were placed 3.4 g of $AlCl_3$ and 1147 g of liquid $Br_2$. A graduated cylinder was charged with 0.10 g of $FeBr_3$ and 59.3 g of $Br_{0.6}$-DPE (prepared in Example 4) which was stirred magnetically. All $FeBr_3$ dissolved after stirring for about 30 minutes. The bromine was brought to reflux and the $Br_{0.6}$-DPE added via the diptube over a period of 2.3 hours, during which the reaction temperature was 58.1-58.2° C. Methylene dibromide (1 mL) was added to the graduated cylinder and pumped into the reaction mixture to clear the diptube. The mixture was held at reflux 34 min. then cooled, 400 mL of tap water was added and the flask was set for distillation. Bromine was distilled to 100° C. After cooling to 62° C., sodium gluconate (0.74 g) was added. The resultant mixture was stirred for about 5 minutes and then 40 g of 25% aqueous NaOH was added. Analysis of the water showed 1.06% NaOH. Added 17 g of additional 25% aqueous NaOH to the mixture. The mixture was filtered and the brominated solids were washed with 200 mL of tap water containing 0.3 g of sodium gluconate followed by 500 mL of deionized water. The washed filter cake was split vertically and one half of the cake (Product A) was oven dried while the other half (Product B) was stirred with 400 mL of hot deionized water containing 12 mL of 60% aqueous HBr. After stirring for about 15 minutes, these solids of Product B were collected and washed with about 500 mL deionized water and oven dried. After drying Products A and B overnight at about 120-130° C., samples of Product A and Product B were analyzed for iron content. It was found that Product A contained 7 ppm of iron and Product B contained 6 ppm of iron.

Example 9

Preparation of Decabromodiphenylethane Product from Partially Brominated DPE, and Purification of the Decabromodiphenylethane Product 1) Scrubbing step—Using the equipment described in Example 1, 0.11 g $FeCl_3$ (anhydrous, black) in 151.8 g of DPE (containing no benzene) was sparged via ⅛-inch (0.32 cm) O.D. diptube with HBr gas saturated at room temperature with $Br_2$ at a rate of about 300 mL/min (30 mL bromine in the flask through which HBr passed). After 3.2 hours all bromine had been evaporated by the HBr gas, during which time the DPE reactor temperature was held at 64-66° C. Without using a $N_2$ purge, 30 mL of water was added to the DPE and the temperature dropped to 59° C. The acidic water phase (10.1% HBr) was separated and the lower organic phase was dried over 2.0 g $CaCl_2$ beads. GC analysis of the product showed 120 ppm of benzene, 40.1% DPE, 51.6% monobromo-DPE, and 7.9% dibromo-DPE.

2) Bromination of Partially Brominated DPE From 1)—In a 2-liter flask equipped with a mechanical stirrer, a thermocouple, a 0° C. Friedrich condenser and a ⅛-inch (0.32 cm) O.D. diptube were placed 5.5 g of $AlCl_3$ and 2310 g of liquid bromine. This mixture was heated to 58° C. and the partially brominated DPE formed in the above scrubbing step was added via the diptube over a period of 5.5 hours during which time the reactor was maintained at 57.3-58° C. The reaction mixture was refluxed 5 minutes longer and then 800 mL of tap water was added and the reaction flask was set for bromine distillation. The bromine was distilled to a temperature of 100° C. and then the mixture was cooled to 60° C. Sodium gluconate (0.30 gram) in 10 mL of water was added and the mixture stirred for 5 minutes. Then, 60 g of 25% aqueous NaOH solution was added. Analysis showed that the NaOH content in the water was 0.9%. An additional 30 g of 25% aqueous NaOH solution was then added and the product solids were collected. The product solids were washed with deionized water to produce a wet filter cake. After drying at 125° C. for three days, the dry weight of the decabromodiphenylethane product was 690 g. Iron analysis showed 0 ppm of iron, i.e., no iron could be detected. A sample, analyzed by GC, showed 0.6 area % $Br_9DPE$ and 99.4% decabromodiphenylethane.

As seen, e.g. from Examples 5, 6, and 9, this invention enables provision of decabromodiphenylethane products produced by bromination of partially brominated diphenylethane in the presence of an iron bromination catalyst, which products have a decabromodiphenylethane assay of at least about 99.4 GC area percent and an iron content in the range of 0 to about 22 ppm. Preferred products of this type also have a Hunter Yellowness Index, using ground or milled samples, of less than about 12.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Each and every patent or publication referred to in any portion of this specification is incorporated in toto into this disclosure by reference, as if fully set forth herein.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

This invention is susceptible to considerable variation in its practice. Therefore the foregoing description is not intended to limit, and should not be construed as limiting, the invention to the particular exemplifications presented hereinabove.

That which is claimed is:

1. A process of removing bromine from a gaseous mixture of bromine and hydrogen bromide, which process comprises passing said gaseous mixture into a mixture having a liquid phase, which mixture is formed from components comprising (i) diphenylethane and/or partially brominated diphenylethane having an average bromine number less than about 2, and (ii) a catalytic quantity of iron and/or at least one iron halide in which the halogen atoms are bromine atoms and/or chlorine atoms, so that component (i) is brominated, and wherein during such bromination, the mixture having a liquid phase is at one or more temperatures at which component (i) and the products formed during the bromination of component (i) are in the liquid state.

2. A process as in claim 1 wherein said mixture having a liquid phase additionally comprises an inert solvent that is in the liquid state during the process.

3. A process as in claim 1 wherein said mixture having a liquid phase is formed essentially entirely from components (i) and (ii), and said mixture having a liquid phase is maintained at one or more temperatures of about 110° C. or below that keep the reaction mixture in the liquid state.

4. A process as in claim 1 wherein said catalytic quantity expressed as iron, is in the range of about 100 to about 5000 parts by weight of iron as (ii) per million parts of (i).

5. A process as in claim 1 wherein immediately before use in forming said mixture, component (i) is diphenylethane.

6. A process as in claim 1 wherein immediately before use in forming said mixture, component (ii) is (a) anhydrous ferric chloride, (b) hydrated ferric chloride, (c) anhydrous ferric bromide, (d) hydrated ferric bromide, or (e) any two or more of (a), (b), (c), (d).

7. A process as in claim 6 wherein said component (ii) is anhydrous ferric chloride, ferric chloride monohydrate, ferric chloride hexahydrate, anhydrous ferric bromide, ferric bromide hexahydrate, or any two or more of them.

8. A process as in claim 1 wherein immediately before use in forming said mixture component (i) is diphenylethane; and wherein immediately before use in forming said mixture, component (ii) is (a) anhydrous ferric chloride, (b) hydrated ferric chloride, (c) anhydrous ferric bromide, (d) hydrated ferric bromide, or (e) any two or more of (a), (b), (c), (d).

9. A process as in claim 8 wherein said component (ii) is anhydrous ferric chloride, ferric chloride monohydrate, ferric chloride hexahydrate, anhydrous ferric bromide, ferric bromide hexahydrate, or any two or more of them.

10. A process as in any of claims 6-9 wherein said catalytic quantity expressed as iron, is in the range of about 100 to about 500 parts by weight of iron as (ii) per million parts of (i).

11. A process as in any of claims 6-9 wherein component (i) in said mixture as formed is diphenylethane or partially brominated diphenylethane having an average bromine number of about 1 or less and wherein in the process said diphenylethane or partially brominated diphenylethane is brominated to an average bromine number of up to about 2.

12. A process of producing a decabromodiphenylethane product, which process comprises:

I) brominating a feed of (A) partially brominated diphenylethane having an average bromine number less than about 4, (B) a mixture of (A) and diphenylethane, or (C) diphenylethane, the bromination being effected with excess bromine in the presence of a Lewis acid bromination catalyst, to produce a decabromodiphenylethane product and wherein a gaseous mixture of hydrogen bromide coproduct containing free molecular bromine is formed, and II) passing at least a portion of said gaseous mixture into a mixture having a liquid phase, which mixture having a liquid phase is formed from components comprising (i) diphenylethane and/or partially brominated diphenylethane having an average bromine number less than about 2 and (ii) a catalytic quantity of an iron-based catalyst which, as initially charged, is iron and/or at least one iron halide in which the halogen atoms are bromine atoms and/or chlorine atoms, the mixture having a liquid phase being at a temperature at which (i) is in the liquid state, whereby (i) is brominated to form a partially brominated diphenylethane having an average bromine number of less than about 4, and the bromine content of said gaseous mixture is reduced or eliminated.

13. A process as in claim 12 wherein said Lewis acid bromination catalyst in the form initially utilized in I) is aluminum and/or an aluminum halide in which the halogen atoms are bromine atoms and/or chlorine atoms and wherein (ii), as initially charged, is (a) anhydrous ferric chloride, (b) hydrated ferric chloride, (c) anhydrous ferric bromide, (d) hydrated ferric bromide, or (e) any two or more of (a), (b), (c), (d).

14. A process as in claim 13 wherein said component (ii), as initially charged, is anhydrous ferric chloride, ferric chloride monohydrate, ferric chloride hexahydrate, anhydrous ferric bromide, ferric bromide hexahydrate, or any two or more of them.

15. A process as in any of claims 12-14 wherein (A) or (B) is brominated in I), and wherein (i) that has been brominated in II) is utilized as all or part of said feed of (A) or (B) in I).

16. A process as in any of claims 12-14 wherein (A) or (B) is brominated in I), wherein component (i) in II) is diphenylethane, and wherein (A) or (B) in I) is diphenylethane that has been brominated in II).

17. A process as in any of claims 12-14 wherein in II) said catalytic quantity of said iron and/or said at least one iron halide is in the range of about 100 to about 5000 parts by weight of iron per million parts of (i).

18. A process as in any of claims 12-14 wherein the bromination in I) is conducted at one or more temperatures in the range of about 50 to about 90° C.

19. A process as in any of claims 12-14 wherein the bromination in II) is conducted at one or more temperatures in the range of about 57 to about 110° C.

20. A process as in any of claims 12-14 wherein the bromination in I) is conducted at one or more temperatures in the range of about 50 to about 90° C. and wherein the bromination in II) is conducted at, independently, one or more temperatures in the range of about 57 to about 110° C.

21. A process of producing a decabromodiphenylethane product, which process comprises:
   1) passing a feed of a gaseous mixture of hydrogen bromide and bromine into a mixture having a liquid phase, which mixture having a liquid phase is formed from components comprising (i) diphenylethane and/or partially brominated diphenylethane having an average bromine number less than about 2 and (ii) a catalytic quantity of iron and/or at least one iron halide in which the halogen atoms as initially charged are bromine atoms and/or chlorine atoms, wherein the mixture having a liquid phase is at one or more temperatures at which (i) is in the liquid state, whereby (i) is brominated so that the amount of bromine in said gaseous mixture is decreased, and a reaction mixture comprising partially brominated diphenylethane having an average bromine number less than about 4 and iron catalyst residues is formed;
   2) feeding at least a portion of said reaction mixture formed in 1) and optionally diphenylethane to a mixture comprising excess liquid bromine, and a Lewis acid bromination catalyst composed of aluminum and/or aluminum halide in which the halogen atoms in the form initially charged are bromine atoms and/or chlorine atoms to produce a bromination reaction mixture comprising a decabromodiphenylethane product, molecular bromine, aluminum catalyst and aluminum catalyst residues, and iron catalyst residues, and to produce as a coproduct, a gaseous mixture of hydrogen bromide and molecular bromine;
   3) deactivating said aluminum catalyst and removing aluminum catalyst residues and iron catalyst residues from said bromination reaction mixture formed in 2), and recovering decabromodiphenylethane product; and
   4) utilizing coproduct gaseous mixture of hydrogen bromide containing molecular bromine as feed in 1).

22. A process as in claim 21 wherein said one or more temperatures in 1) are in the range of about 57 to about 100° C., wherein said reaction mixture in 2) is, independently, at one or more temperatures in the range of about 50 to about 90° C., and wherein diphenylethane and at least a portion of said reaction mixture formed in 1) are fed in 2).

23. A process as in claim 21 wherein in 1) component (i) used in forming said mixture having a liquid phase is diphenylethane.

24. A process as in claim 21 wherein in 1) component (ii) used in forming said mixture having a liquid phase is anhydrous ferric chloride, ferric chloride monohydrate, ferric chloride hexahydrate, anhydrous ferric bromide, or ferric bromide hexahydrate, or any two or more of them.

25. A process of producing a decabromodiphenylethane product which process comprises:
   I) brominating a feed of (A) partially brominated diphenylethane having an average bromine number less than about 4, (B) a mixture of (A) and diphenylethane, or (C) diphenylethane, the bromination being effected with excess bromine in the presence of a Lewis acid bromination catalyst to produce a decabromodiphenylethane product and wherein a gaseous mixture of hydrogen bromide coproduct containing free molecular bromine is formed;
   II) passing at least a portion of said gaseous mixture into a liquid mixture formed from components comprising (i) diphenylethane and/or partially brominated diphenylethane having an average bromine number less than about 2 and (ii) a catalytic quantity of an iron-based catalyst which, as initially charged, is iron and/or at least one iron halide in which the halogen atoms are bromine atoms and/or chlorine atoms, the liquid mixture being at a temperature at which (i) is in the liquid state, whereby (i) is brominated to form a reaction mixture comprising partially brominated diphenylethane having an average bromine number of less than about 4 and iron catalyst residues, and the bromine content of said gaseous mixture is reduced or eliminated;
   III) removing iron catalyst residues from reaction mixture formed in II); and
   IV) utilizing as (A) in I), at least a portion of reaction mixture of III) from which iron catalyst residues have been removed in III).

26. A process as in claim 25 wherein III) comprises adding water to said reaction mixture formed in II), phase separating the water, drying the organic phase with a desiccant.

27. A process as in claim 25 wherein III) comprises washing said reaction mixture with water to form a two phase mixture, phase separating the water, and if the water content is above about 400 ppm, drying the organic phase with a desiccant.

28. A process as in claim 26 or 27 wherein said desiccant is calcium chloride.

29. A process as in claim 25 wherein in I) said Lewis acid bromination catalyst as initially charged is aluminum metal or aluminum halide in which the halogen atoms are bromine atoms or chlorine atoms, or both, and wherein in II) said iron-based catalyst as initially charged is (a) anhydrous ferric chloride, (b) hydrated ferric chloride, (c) anhydrous ferric bromide, (d) hydrated ferric bromide, or (e) any two or more of (a), (b), (c), (d).

30. A process as in claim 29 wherein said iron-based catalyst as initially charged is anhydrous ferric chloride, ferric chloride monohydrate, ferric chloride hexahydrate, anhydrous ferric bromide, or ferric bromide hexahydrate, or any two or more of them.

* * * * *